US00PP14272P29

(12) United States Plant Patent
Hanes

(10) Patent No.: US PP14,272 P2
(45) Date of Patent: Nov. 4, 2003

(54) PETUNIA PLANT NAMED 'JAM CHEROSE'

(50) Latin Name: *Petunia hybrida*
Varietal Denomination: Jam Cherose

(75) Inventor: Mitchell Eugene Hanes, Morgan Hill, CA (US)

(73) Assignee: Goldsmith Seeds Inc., Gilroy, CA (US)

( * ) Notice: Subject to any disclaimer, the term of this patent is extended or adjusted under 35 U.S.C. 154(b) by 0 days.

(21) Appl. No.: 10/389,103

(22) Filed: Mar. 13, 2003

(51) Int. Cl.[7] ..... A01H 5/00
(52) U.S. Cl. ..... Plt./356
(58) Field of Search ..... Plt./356

*Primary Examiner*—Kent Bell
(74) *Attorney, Agent, or Firm*—Jondle & Associates P.C.

(57) ABSTRACT

A petunia cultivar particularly distinguished by red-purple colored flowers, compact habit and good basal branching.

1 Drawing Sheet

Genus and species: Petunia hybrida.
Variety denomination: 'Jam Cherose'.

BACKGROUND OF THE NEW PLANT

The present invention comprises a new and distinct cultivar of petunia, botanically known as Petunia hybrida, and hereinafter referred to by the cultivar name 'Jam Cherose'. The new cultivar is asexually reproduced from vegetative cuttings and tissue culture resulting from the cross of the pollen parent 'Red Horizon', a commercial seed propagated variety that is unpatented ×99-220-17, a double purple proprietary line that is unnamed and unpatented.

'Jam Cherose' is a product of a planned breeding program intended to create new petunia plants with Red-Purple colored flowers, compact habit, good basal branching and moderately vigorous growth.

The new cultivar was created in 1999 in Gilroy, Calif. and has been asexually reproduced repeatedly by vegetative cuttings and tissue culture in Gilroy, Calif., Andijk, The Netherlands, and Guatemala over a three-year period. The plant has also been trialed at Gilroy, Calif., Litchfield, Mich. and Andijk, The Netherlands. The present invention has been found to retain its distinctive characteristics through successive asexual propagations; and this novelty is firmly fixed.

DESCRIPTION OF PHOTOGRAPH

This new petunia plant is illustrated by the accompanying photograph which shows blooms, buds, and foliage of the plant in full color, the colors shown being as true as can be reasonably obtained by conventional photographic procedures.

The Photograph shows the mature flowers.

DESCRIPTION OF THE NEW CULTIVAR

The following detailed descriptions set forth the distinctive characteristics of 'Jam Cherose'. The data, which defines these characteristics, were collected from asexual reproductions carried out in Gilroy, Calif. The plant history was taken on 5 months old plants grown in one-gallon pots in fall/winter season, in a poly-covered greenhouse under 2–4 supplemental light and color readings were taken in the greenhouse in the winter season under natural light. Plants had been cut back numerous times prior to data readings taken. Color references are primarily to The R.H.S. Colour Chart of The Royal Horticultural Society of London (R.H.S.). Texture description details were observed under a dissecting microscope according to The New Royal Horticultural Society Dictionary of Gardening (1992).

THE PLANT

Classification:
*Botanical.*—Petunia hybrida.
*Commercial.*—Petunia.
Form: Semi upright and decumbent.
Growth and branching habit: Good vigorous habit, well-branched, full plant.
Height: From soil level to top of blooms: Approximately 20–25 cm.
Width: Approximately 40–50 cm including flowers.
Time to produce a finished flowering plant: 9–11 weeks.
Outdoor plant performance: Full sun, free- flowering through the summer, some heat tolerance. Use as a hanging plant, mixed containers, window boxes and mass plantings.
Time to initiate roots: Approximately 18–23 days in the greenhouse.
Root description: Fibrous, white.

THE LEAVES

Arrangement: Alternate, upper leaves sub-opposite.
Length: 5.5–6.0 cm.
Width: 2.7–3.7 cm.
Leaf blade shape: Ovate to Elliptic.
Leaf margin: Entire.
Apex aspect: Acute.
Base aspect: Acuminate.
Leaf color: Upper side; RHS 137A (green); Underside; RHS 138A (green).
Texture: Short glandular hairs.
Venation: Palmate.
Venation color: RHS 144B (yellow-green).
Petiole length: 0.30–0.50 cm.
Petiole width: 0.20 cm.
Petiole color: RHS 144B (yellow-green).
Petiole texture: Short glandular hairs.

THE STEM

Length: 30 cm.
Diameter: 0.3–0.45 cm.
Internode length: 1.0–3.0 cm.
Color: RHS 144A (yellow-green).
Texture: Long glandular hair.
Stem anthocyanin: None.
Peduncle color: RHS 144B (yellow-green).
Peduncle length: 6.0–7.5 cm.
Peduncle diameter: 0.15 cm.
Peduncle texture: Many glandular hairs of various sizes.

THE BUD

Shape: Oblong.
Diameter: 0.5 cm.
Length: 2.5–4.0 cm.
Color at tight bud: RHS 59A (red-purple).

THE FLOWER

Blooming habit: Continuous throughout the growing season. Good floriferousness.
Inflorescence type: Flowers solitary in upper leaf axis.
Young flower color: In between RHS 60A/B (red-purple), but a little brighter.
Young flower floret diameter: 4.4–4.7 cm.
Mature flower color: Front side, between RHS 60A/B (red-purple), a little brighter, weak RHS 59B (red-purple) veining. Underside, RHS 61B (red-purple); RHS 166A (greyed-orange) mid vein.
Corolla tube color inside: Back of corolla throat is RHS 142D (green); RHS N74D (red-purple) towards the petal flare; RHS 176B (greyed-orange) veining throughout.
Corolla tube length: 2.5–2.8 cm (calyx to the petal flare).
Corolla outside texture: Many glandular hairs.
Floret form and number of petals: 5 lobed petals (single type) fused at base.
Flower (limb) diameter: 5.5–5.8 cm.
Petal apex shape: Praemorse.
Petal margin: Entire.
Petal waviness (ruffle of petals): Weak.
Petal lobation: Moderate.
Petal texture: Papillose.
Calyx: 5, sometimes 6 deeply lobed sepals, fused at base.
Sepal color: RHS 137B (green).
Sepal length: 1.9–2.3 cm.
Sepal width: 0.5–0.7 cm.
Sepal shape: Oblong.
Sepal apex: Obtuse.
Sepal texture: Short glandular hairs.
Lastingness of individual blooms: 4–8 days.
Fragrance: Slightly sweet.

THE REPRODUCTIVE ORGANS

Stamens: 5, 2 taller and 3 shorter.
Filament color: RHS N155D (white) with a hint of RHS 70B (red-purple) under the anthers.
Pollen color: RHS 11C (yellow).
Pistil: One.
Stigma: RHS 144A (yellow-green).
Style color: RHS 144D (yellow-green).
Fruit seed set: Not observed.

DISEASE AND INSECT RESISTANCE

Not observed.

COMPARISON WITH KNOWN CULTIVARS

Compared to its female parent 99-220-17 in the following ways: The female parent has a purple flower color vs. a cherry rose. The female parent has a double flower form vs. a single flower form and the female parent is later to flower.

Compared to its male parent 'Red Horizon' in the following ways: Red vs. cherry rose flower color. 'Red Horizon' has a more upright plant growth habit than 'Jam Cherose', which is flatter growing.

I claim:

1. A new and distinct petunia plant as shown and described herein.

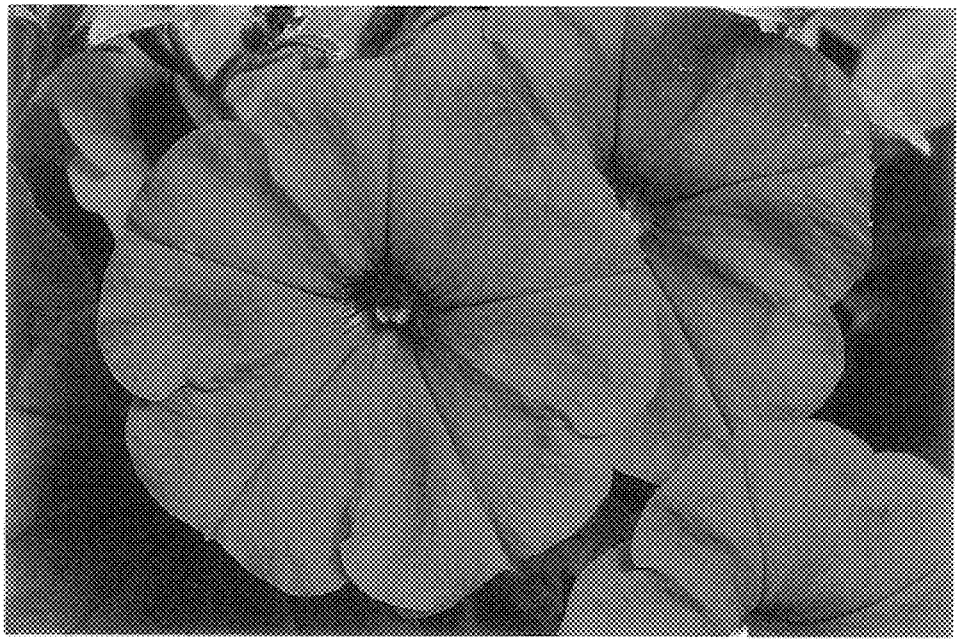

* * * * *